US008551095B2

(12) United States Patent
Fritzinger et al.

(10) Patent No.: US 8,551,095 B2
(45) Date of Patent: Oct. 8, 2013

(54) BONE PLATE HAVING COMBINATION LOCKING AND COMPRESSION SCREW HOLES

(75) Inventors: Daniel Duane Fritzinger, Warsaw, IN (US); Paul G. Kiritsis, Midlothian, VA (US)

(73) Assignee: Bionet Manufacturing, LLC, Warsaw, IN (US)

( * ) Notice: Subject to any disclaimer, the term of this patent is extended or adjusted under 35 U.S.C. 154(b) by 218 days.

(21) Appl. No.: 13/019,639

(22) Filed: Feb. 2, 2011

(65) Prior Publication Data

US 2012/0197307 A1    Aug. 2, 2012

(51) Int. Cl.
*A61B 17/58* (2006.01)
*A61B 17/80* (2006.01)

(52) U.S. Cl.
USPC .............................................. 606/70; 606/280

(58) Field of Classification Search
USPC ....................................... 606/70–71, 280–299
See application file for complete search history.

(56) References Cited

U.S. PATENT DOCUMENTS

| 3,668,972 | A | * | 6/1972 | Allgower et al. ............. 409/132 |
| 4,493,317 | A | * | 1/1985 | Klaue ............................ 606/282 |
| 4,513,744 | A | | 4/1985 | Klaue |
| 5,709,686 | A | | 1/1998 | Talos et al. |
| 6,001,099 | A | * | 12/1999 | Huebner ........................ 606/281 |
| 6,669,701 | B2 | | 12/2003 | Steiner et al. |
| 6,719,759 | B2 | | 4/2004 | Wagner et al. |
| 6,730,091 | B1 | * | 5/2004 | Pfefferle et al. ................ 606/70 |
| 2007/0083207 | A1 | * | 4/2007 | Ziolo et al. ...................... 606/73 |
| 2008/0249572 | A1 | * | 10/2008 | Tandon .......................... 606/280 |
| 2009/0318921 | A1 | * | 12/2009 | White et al. .................... 606/70 |
| 2010/0137692 | A1 | * | 6/2010 | Lindsay et al. ............... 600/235 |

OTHER PUBLICATIONS

Zimmer Universal Locking System Brochure, 2009 (2 pages).
Synthes Locking Compression Plate (LCP) Brochure, 2003 (6 pages).

* cited by examiner

*Primary Examiner* — Todd Manahan
*Assistant Examiner* — Eric S Gibson
(74) *Attorney, Agent, or Firm* — Ryan O. White; Taft Stettinius & Hollister LLP (57) ABSTRACT

A bone plate including a combination locking and compression screw hole having a top opening and a bottom opening, the top opening being generally circular and including a widthwise dimension and a lengthwise dimension normal to the widthwise dimension, where an interior wall of the bone plate extends between the top opening and the bottom opening, where at least a portion of the interior wall proximate the top opening is threaded, and where at least one of the widthwise dimension and the lengthwise dimension is decreased between the top opening to the bottom opening, while the other of the widthwise dimension and the lengthwise dimension does not substantially decrease between the top opening and the bottom opening. The instant disclosure also includes a method of forming a bone plate comprising: (a) fabricating a bone plate to include a first through hole, where at least one of a width and a length of the hole changes along a depth of the hole; (b) plunge milling an interior surface of the bone plate demarcating the first through hole to remove at least a portion of the bone plate to increase at least one of the width and the length of the through hole; and (c) threading at least a portion of the first through hole.

9 Claims, 7 Drawing Sheets

BONE PLATE HAVING COMBINATION LOCKING AND COMPRESSION SCREW HOLES

RELATED ART

1. Field of the Invention

The present disclosure is directed to bone plates and, more specifically, to bone plates having fastener holes that may be utilized as locking holes or as compression holes, depending upon the initial placement of the fastener with respect to the fastener hole.

2. Brief Discussion of Related Art

Bone plates used in conjunction with screws to fix bone fractures often contain locking screw holes and compression slots. Locking screw holes provide additional plate-to-screw fixation to lock bone fragments in place and aid in healing of bone fractures. Compression slots, on the other hand, are used to compress the ends of bone fragments together to aid in primary healing.

Typically, a bone plate includes at least one locking screw hole and at least one compression slot. The location of the holes and slots dictate the locations on the bone plate where the surgeon can apply locking or compression forces.

INTRODUCTION TO THE INVENTION

The present invention is directed to bone plates having fastener holes that may be utilized as locking holes or as compression holes, depending upon the initial placement of the fastener with respect to the fastener hole. By providing a single hole that can act as a compression hole or a locking hole, the bone plate provides a surgeon with greater flexibility as to the placement of locking fasteners and compression fasteners in a smaller footprint than in a traditional plate having dedicated space for each type of hole.

It is a first aspect of the present invention to provide a bone plate including a hybrid through screw hole, where the hybrid through screw hole includes a top opening and a bottom opening, the top opening being generally circular and including a widthwise dimension and a lengthwise dimension normal to the widthwise dimension, where an interior wall of the bone plate extends between the top opening and the bottom opening, where at least a portion of the interior wall proximate the top opening is threaded, and where at least one of the widthwise dimension and the lengthwise dimension is decreased between the top opening to the bottom opening, while the other of the widthwise dimension and the lengthwise dimension does not substantially decrease between the top opening and the bottom opening.

In a more detailed embodiment of the first aspect, the interior wall includes a first portion having a first circumferential curvature and a second portion having a second circumferential curvature, wherein the first circumferential curvature is larger than the second circumferential curvature. In yet another more detailed embodiment, the second portion does not include threads. In a further detailed embodiment, the first portion is at least one of arcuate and tapered in the vertical direction and, the second portion includes a vertical wall. In still a further detailed embodiment, the interior wall includes a first portion having a first circumferential curvature, a second portion having a second circumferential curvature, and a third portion having a third circumferential curvature, wherein the first circumferential curvature is larger than the second circumferential curvature and the third circumferential curvature. In a more detailed embodiment, the second portion is opposite the third portion. In a more detailed embodiment, the second circumferential curvature is generally the same as the third circumferential curvature. In another more detailed embodiment, the first portion includes threads, the second portion does not include threads and, the third portion does not include threads. In yet another more detailed embodiment, the first portion is at least one of arcuate and tapered in the vertical direction, the second portion includes a vertical, wall and, the third portion includes a vertical wall.

It is a second aspect of the present invention to provide a bone plate comprising a combination compression and locking through hole, where the combination hole includes a first portion having a circular, horizontal cross-section and a second portion having an oblong, horizontal cross-section, where the circular, horizontal cross-section and the oblong, horizontal cross-section lie along differing planes perpendicular to a central axis extending through the combination compression and locking through hole.

In a more detailed embodiment of the second aspect, the bone plate further includes a plurality of combination compression and locking through holes, where each of the plurality of combination compression and locking through holes includes a first portion including a circular, horizontal cross-section and a second portion including an oblong, horizontal cross-section. In yet another more detailed embodiment, the combination compression and locking through hole is at least partially threaded. In a further detailed embodiment, the first portion is threaded and the second portion is unthreaded. In still a further detailed embodiment, the first portion includes a diameter D, the second portion includes a maximum length L and, the diameter D is approximately equal to the length L.

It is a third aspect of the present invention to provide a bone plate comprising a through screw hole demarcated by an interior surface of the bone plate that extends between a top opening and a bottom opening, the top opening having a continuous arcuate shape and allowing throughput of a first imaginary cylinder having a circular cross-section with a diameter D1, the interior surface having a first segment that is at least partially threaded and tapers to a stopping distance SD to inhibit throughput of the first imaginary cylinder at a location between the top opening and the bottom opening, the interior surface having a second segment adjacent to the first segment, the first segment and the second segment allowing throughput of a second imaginary cylinder having a circular cross-section with a diameter D2, where the diameter D1 is greater than the diameter D2, where the stopping distance SD is greater than D2, and wherein a maximum horizontal distance across the second segment is greater than 1.3 times D2.

In a more detailed embodiment of the third aspect, the interior surface of the first segment includes a first circumferential curvature and the second segment includes a second circumferential curvature, wherein the first circumferential curvature is larger than the second circumferential curvature. In yet another more detailed embodiment, the second segment does not include threads. In a further detailed embodiment, the first segment is at least one of arcuate and tapered in the vertical direction and, the second segment includes a vertical wall. In still a further detailed embodiment, the interior surface includes a first segment having a first circumferential curvature, the second segment includes a second portion having a second circumferential curvature and a third portion having a third circumferential curvature, wherein the first circumferential curvature is larger than the second circumferential curvature and the third circumferential curvature. In a more detailed embodiment, the second portion lies generally opposite the third portion. In a more detailed embodiment, the second circumferential curvature is generally the same as the third circumferential curvature. In another more detailed embodiment, the first portion includes threads, the second portion does not include threads and, the third portion does not include threads. In yet another more detailed embodiment, the first portion is at least one of arcuate and tapered in the vertical direction, the second portion includes a vertical wall and, the third portion includes a vertical wall.

It is a fourth aspect of the present invention to provide a method of forming a bone plate comprising: (a) fabricating a bone plate to include a first through hole, where at least one of a width and a length of the hole changes along a depth of the hole; (b) plunge milling an interior surface of the bone plate demarcating the first through hole to remove at least a portion of the bone plate to increase at least one of the width and the length of the through hole; and (c) threading at least a portion of the first through hole.

In a more detailed embodiment of the fourth aspect, threading at least a portion of the first through hole occurs before the plunge milling act. In yet another more detailed embodiment, threading at least a portion of the first through hole occurs after the plunge milling act. In a further detailed embodiment, the length and width of the through hole at a top surface of the bone plate are identical. In still a further detailed embodiment, the length and width of the through hole at a bottom surface of the bone plate are identical after the fabricating act and, the length and width of the through hole at the bottom surface of the bone plate are not identical after the plunge milling act. In a more detailed embodiment, the plunge milling act includes using an end mill to remove material in a cylindrical swath, a first axis extends through a center of the through hole, a second axis extends through a circular center of the cylindrical swath and, the first axis is parallel with the second axis. In a more detailed embodiment, the plunge milling act includes using an end mill to remove material in a cylindrical swath, the plunge milling act includes applying the cylindrical swath to opposing ends of the through hole to create a first cylindrical swath and a second cylindrical swath, the first cylindrical swath includes a first axis extending through a circular center thereof, the second cylindrical swath includes a second axis extending through a circular center thereof, the first axis is parallel with the second axis and, the first axis is offset from the second axis.

It is a fifth aspect of the present invention to provide a method of forming a bone plate comprising fabricating a bone plate to include a combination compression and locking hole, where the combination compression and locking hole includes a first portion having a circular cross-section and a second portion having an oblong cross-section, where the circular cross-section and the oblong cross-section lie along differing planes perpendicular to a central axis extending through the combination compression and locking hole.

In yet another more detailed embodiment of the fifth aspect, the fabricating step includes machining a bone plate from a solid block of material. In still another more detailed embodiment, a first portion of the hole tapers to reduce a cross-sectional area of the hole. In a further detailed embodiment, the fabricating step includes forming threads within an interior surface of the bone plate demarcating the hole. In still a further detailed embodiment, the fabricating step includes removing some of the bone plate to increase at least one of a width and a length of the hole after the hole has been formed.

DETAILED DESCRIPTION

The exemplary embodiments of the present disclosure are described and illustrated below to encompass bone plates and, more specifically, to bone plates having fastener holes that may be utilized as locking holes or as compression holes, depending upon the initial placement of the fastener with respect to the fastener hole. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
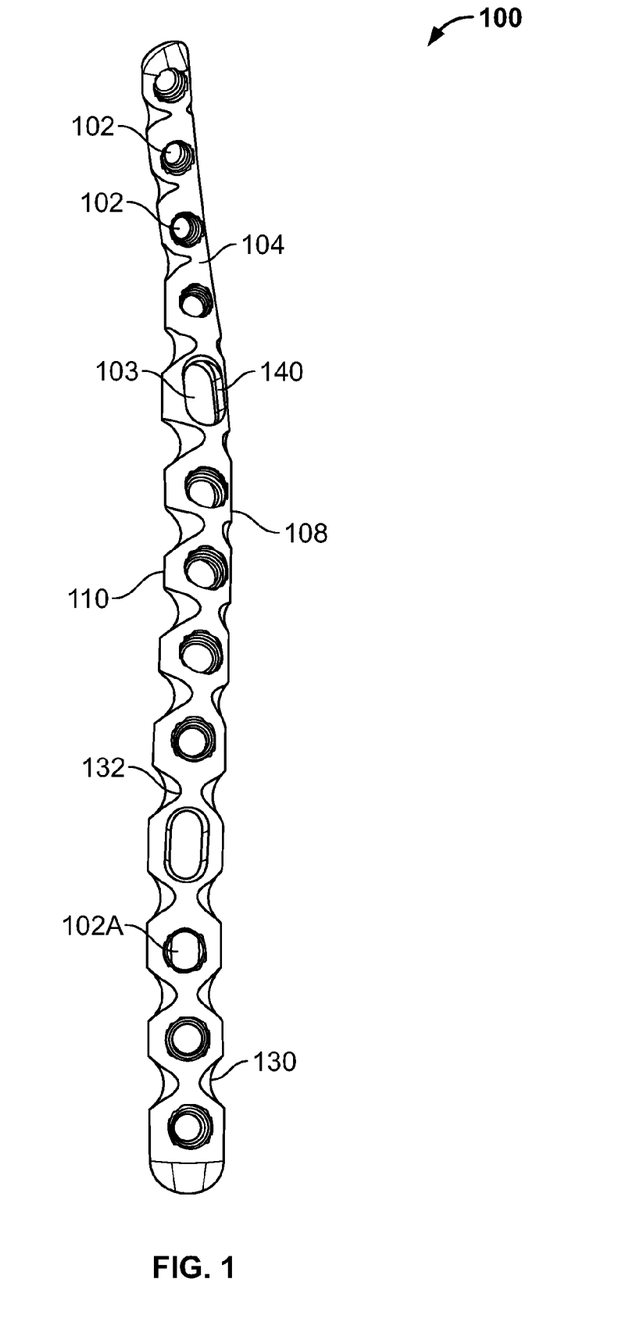
FIG. 1 is an elevated perspective view of an exemplary bone plate incorporating at least one combination locking and compression screw hole.

Referencing FIG. 1, an exemplary bone plate 100 comprises a clavicle bone plate. This clavicle bone plate 100 includes an elongated, longitudinal dimension that includes a series of fastener holes 102, 103, 102A distributed in a spaced-apart fashion along the longitudinal length. Each fastener hole 102, 103, 102A extends between the top surface 104 and bottom surface 106. In this exemplary embodiment, the top surface 104 is generally convex from superior to inferior, while the bottom surface 106 is generally concave from superior to inferior. This shape is operative to form a channel defined by the bottom surface 106 that is adapted to receive a biologic substrate, such as bone. And each fastener hole 102, 103, 102A is generally centered between a superior side 108 and an inferior side 110.

In this exemplary embodiment, the fastener holes 102, 103, 102A generally take on three forms. A first form hole 102 includes a generally circular through opening that extends between the top and bottom surfaces 104, 106. This first form hole 102 has a horizontal circular cross-section that changes in diameter in order to provide a taper in the hole, with the taper being located proximate the bottom surface. It should be noted, however, that wherever a horizontal cross-section of this first hole 102 is taken, the cross-section will be circular. In order to form this hole, a milling machine (not shown) uses an end mill to remove material from the bone plate in order to form the interior wall that defines the through hole. As part of this first form hole 102, the milling machine removes material from the hole to create a taper from top to bottom so that the area of the horizontal, circular cross-sections at some point between the top and bottom decreases. After the milling machine has formed the hole, the wall of the hole is relatively smooth. Thereafter, a threading procedure is carried out to form threads on the interior of the hole 102. These threads, however, do not generally change the circular cross-section of the hole. But the second form hole 103 does not include a horizontal circular cross-section.

In contrast to the first hole 102, the second form hole 103 includes an elongated shape having a non-circular cross-section. By way of example, the second form hole 103 includes a longitudinal dimension that is greater than a widthwise dimension (superior to inferior). At the top of the second form hole 103, proximate the top surface 104, the longitudinal dimension accommodates multiple longitudinal positions for a screw (such as a locking screw 180 or a compression screw 210). But the widthwise dimension is generally uniform and allows for positioning of the screw in only a single widthwise position. In other words, the second form hole 103 allows for positioning the screw in a number of longitudinal positions, but the position of the screw in the superior-to-inferior (i.e., widthwise) direction is generally not amendable to multiple positions. Similarly, the first form hole 102 does not allow for multiple positions of the screw in the inferior-to-superior direction. But, conversely to the second form hole 103, the first form hole 102 fails to allow multiple positions of the screw in the longitudinal direction.

The two screw form holes 102, 103 also differ in that the first form hole 102 is threaded, while the second form hole 103 is not threaded. In order to retain the screw within the second form hole 103, a circumferential flange 140 (recessed in between the top and bottom surfaces 104, 106) extends into the hole and is operative to decrease the through hole diameter enough so that throughput of the screw head is retarded. Because of the longitudinal position variance provided by the second form hole 103, compression screws 210 are more commonly inserted into this hole, as opposed to locking screws 180. As would be expected, the threaded nature of the first form hole 102 results in locking screws 180 being inserted into these holes more commonly than compression screws 210.

Figure 2:
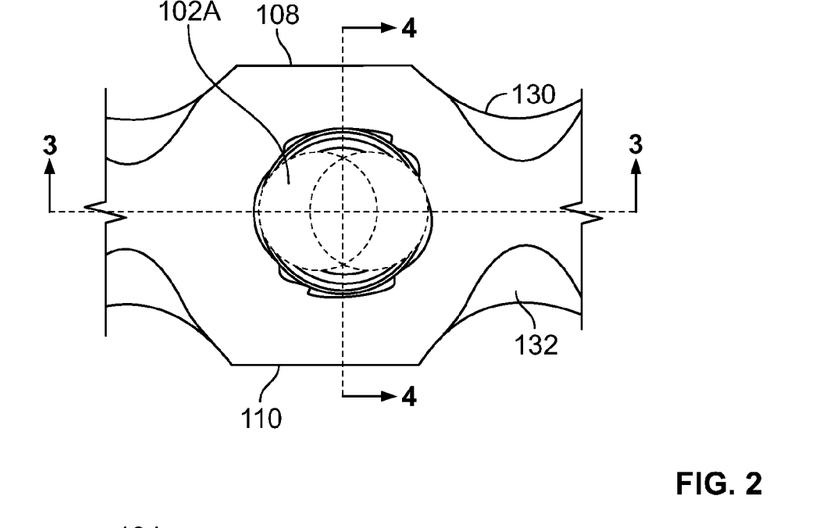
FIG. 2 is an overhead view of the exemplary combination locking and compression screw hole shown in FIG. 1.

A third form hole 102A comprises a hybrid hole that may be utilized as a locking screw hole or as a compression screw hole. In exemplary form, the hybrid fastener hole 102A includes a circular cross-section at the top surface 104 and an oblong cross-section at the bottom surface 106. More specifically, the oblong cross-section of the hole 102A at the bottom surface 106 includes a first, larger dimension 112 running longitudinally along the longitudinal dimension of the hole 102A, and a second, smaller dimension 114 running inferiorly between the superior and inferior sides 108, 110. It should be noted that the larger dimension 112 is approximately the same as the diameter of the hole 102A at the top surface 104. In this exemplary embodiment, the larger dimension 112 is 0.205 inches, while the smaller dimension is 0.145 inches. Those skilled in the art will understand that differing dimensions (greater or lesser) are well within the scope of the invention.

Figure 3:
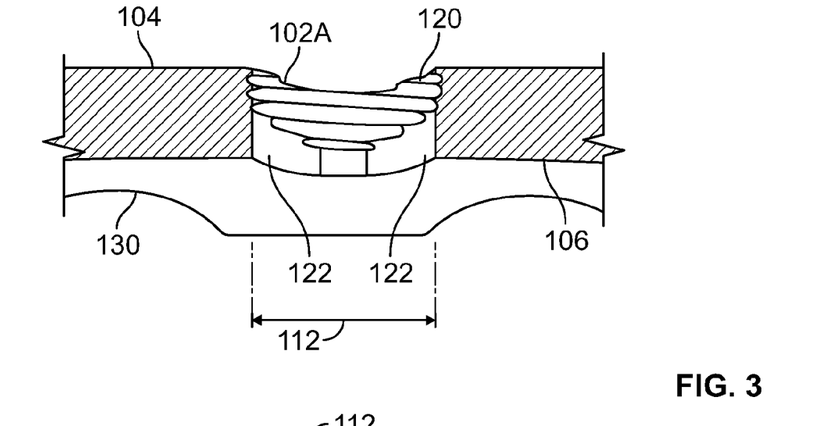
FIG. 3 is a cross-sectional view taken along line C in FIG. 2.
Figure 4:
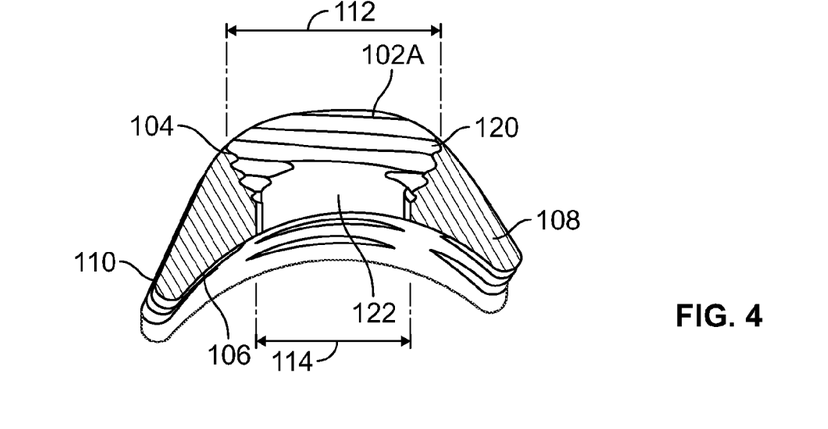
FIG. 4 is a cross-sectional view takes along line B in FIG. 2.

Located between the top and bottom surfaces 104, 106 for the first and third form holes 102, 102A are helical threads 120 that extend from portions of an interior wall 122 to delineate the vertical cross-section of each hole 102A. The interior wall 122 takes on a general shape that resembles a bowl or a frustum, where portions of the interior wall 122 departing from the bowl or frustum shape may not include the helical threads 120.

An exterior of the bone plate 100 includes a number of indentations 130 that are formed into the superior and inferior sides 108, 110. Each indentation 130 is located opposite another indentation so that a pair of indentations generally interposes consecutive fastener holes 102, 102A. In this exemplary embodiment, each indentation 130 operates to decrease the widthwise dimension (superior 108 to inferior 110) of the bone plate 100, while at the same time cooperating with arcuate depressions 132 to decrease the thickness (top surface 104 to bottom surface 106) of the bone plate. Specifically, the arcuate depressions 132 extend along the top surface 104 and terminate just shy of the superior-inferior midline extending longitudinally along the length of the bone plate 100.

To fabricate the exemplary bone plate 100, a solid block of metal (e.g., stainless steel, titanium, etc.) is milled to form the general shape of the bone plate. This includes milling the bone plate 100 to have the requisite length, width, and thickness, in addition to providing a top surface 104 that is convex and a bottom surface 106 that is concave along the longitudinal length. In addition, the milling is operative to form the indentations 130 and remove material from the bone plate 100 in order to form the depressions 132. After the general shape of the bone plate is finished, the fastener holes of the first and second form 102, 103 are formed through the bone plate 100.

Figure 5:
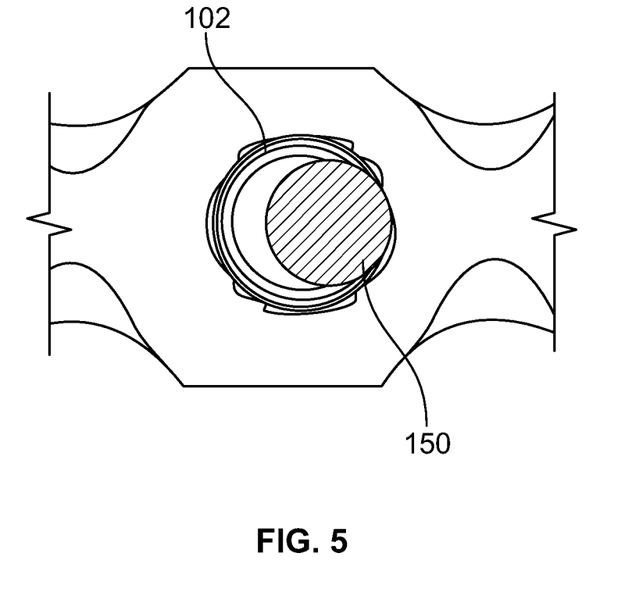
FIG. 5 is an overhead view of a locking screw hole while a portion is bored out using an end mill.
Figure 6:
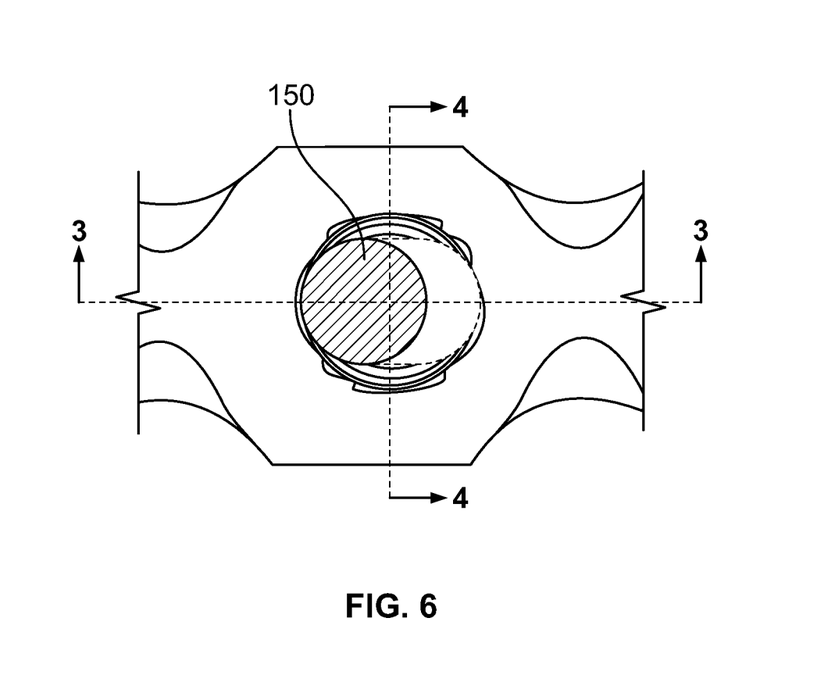
FIG. 6 is an overhead view of the locking screw hole of FIG. 5, with an opposing portion being bored out using an end mill to form the combination locking and compression screw hole.

Referring to FIGS. 5 and 6, in order to form the hybrid holes 102A, an additional step is taken to modify one or more of the first form holes 102. Specifically, a milling machine is utilized to carry out a plunge down operation on the first form hole 102 that removes a portion of the internal threads and interior wall in the longitudinal direction to create an oblong opening at the bottom of the hole. As discussed previously, the first form hole 102 has a diameter of 0.205 inches (and a circumferential curvature that matches this 0.205 inch diameter) at the top surface 104 and a diameter of 0.145 inches at the bottom surface 106 prior to the plunge down operation. After the plunge down operation is complete, the diameter of 0.205 inches at the top surface 104 remains unchanged, while the longitudinal dimension of the hole at the bottom surface 106 is changed to create an oblong shape. Specifically, the plunge down operation creates an oblong hole at the bottom surface 106 having a longitudinal dimension of 0.205 inches, while maintaining the widthwise dimension of 0.145 inches.

The plunge down operation involves using an end mill 150 having an outside diameter of 0.138 inches, where the end mill is oriented in parallel to the through axial center of the hole and is longitudinally offset 0.03 inches from this axial center, but is centered in the superior-to-inferior direction. In a first plunge down operation (see FIG. 5), the end mill 150 is longitudinally offset 0.03 inches in the proximal direction and removes a portion of the interior surface to create a wall having a circumferential curvature of a circle having a diameter of 0.138 inches. In a second plunge down operation, the end mill 150 is longitudinally offset 0.03 inches in the distal direction (see FIG. 6) and removes another portion of the interior surface to create another wall having a circumferential curvature of a circle having a diameter of 0.138 inches. The result of the plunge down operation is a hole 102A having hybrid characteristics to accept either a locking or compression screw 180, 210 without sacrificing the functionality of a locking screw or the functionality of a compression screw.

Figure 7:
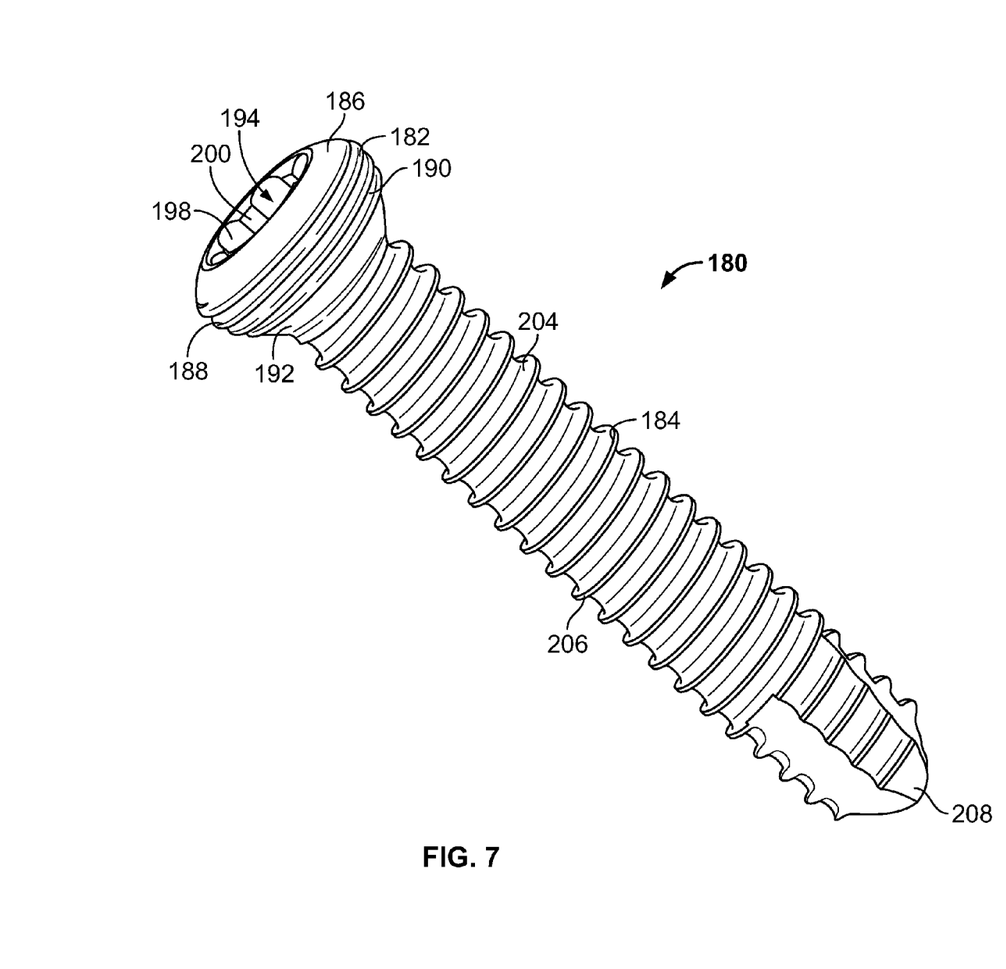
FIG. 7 is an elevated perspective view of an exemplary locking screw.
Figure 8:
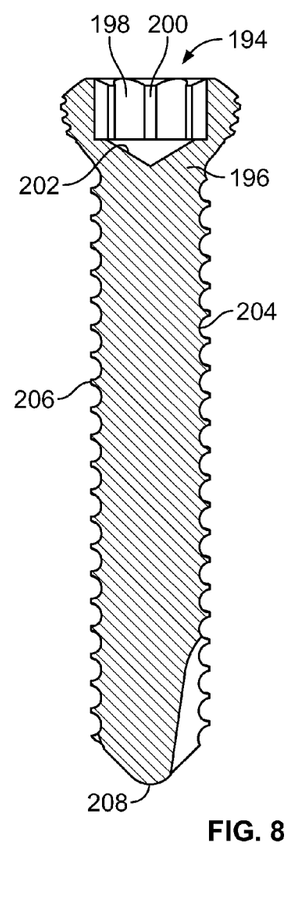
FIG. 8 is a vertical cross-section of the exemplary locking screw of FIG. 7 taken at the middle.

Referring to FIGS. 7 and 8, an exemplary locking screw 180 includes a head 182 and a shaft 184 extending from the head. The head 182 comprises a dome 186 that transitions into an arcuate circumferential surface 188 that includes helical threads 190 adapted to engage the threads 120 of the bone plate holes 102, 102A. The circumferential surface 188 transitions into an underneath planar surface 192 at the bottom of the head 182 to take on a frustum profile. Opposite the bottom of the head 182 is an opening 194 formed at the apex of the dome 186. The opening 194 extends through the head 182 and into a head end 196 of the shaft 184. In exemplary form, the opening 194 is defined by a series of six alternating semicircular walls 198 and six straight walls 200 that form a hexagonal pattern. At the base of the walls 198, 200 is a conical wall 202 that defines a conical part of the opening 194 terminating in the head end 196 of the shaft 184. An exterior surface 204 of the shaft 184 includes helical threads 206 that are adapted to engage a biologic substrate (not shown), such as bone. The threads 206 extend along the shaft until reaching a pointed projection 208 at a far end of the screw 180.

Figure 9:
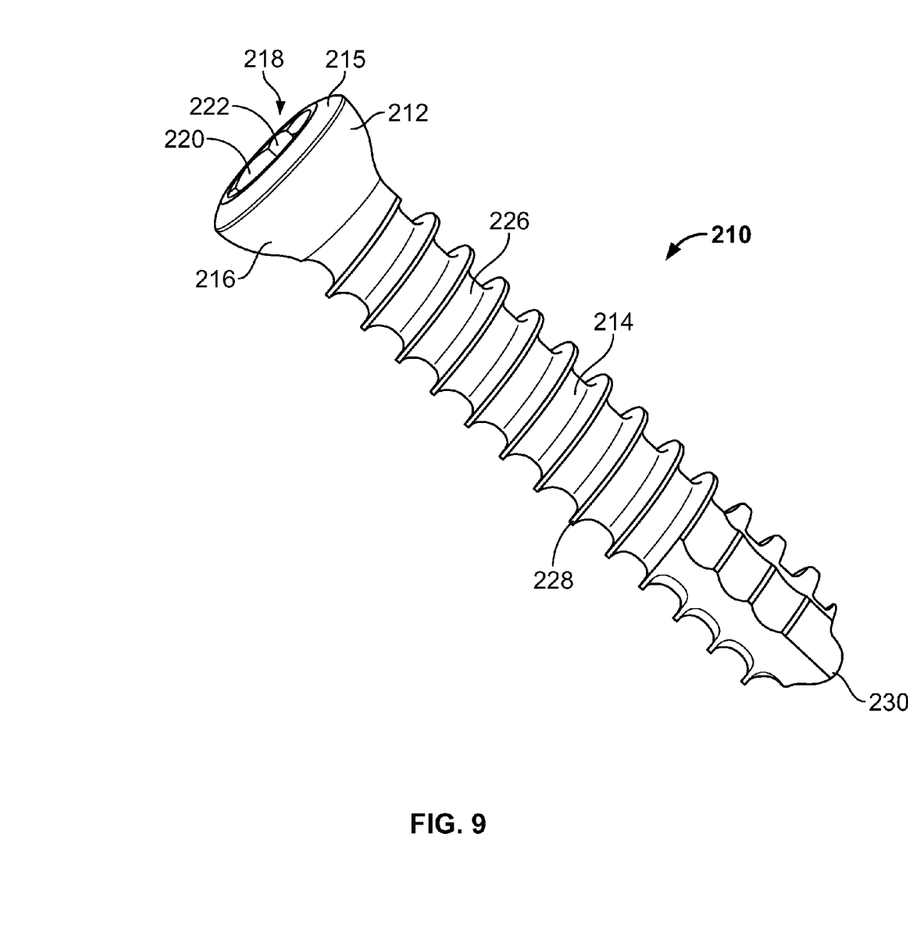
FIG. 9 is an elevated perspective view of an exemplary compression screw.
Figure 10:
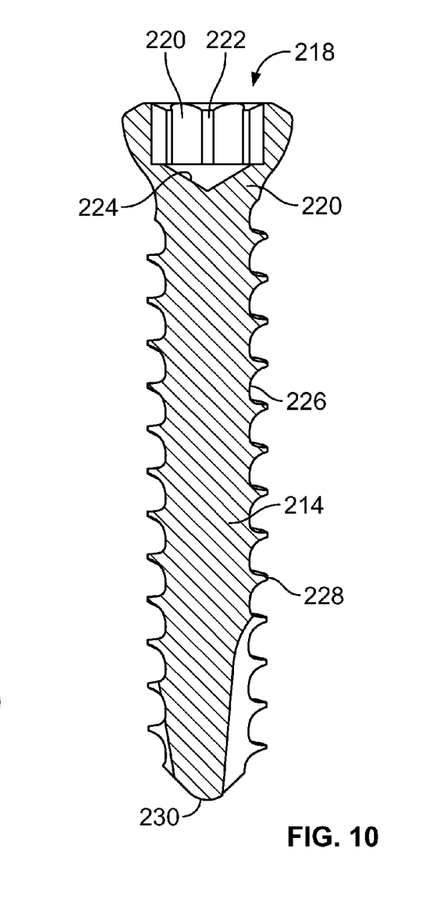
FIG. 10 is a vertical cross-section of the exemplary compression screw of FIG. 9 taken at the middle.

Referencing FIGS. 9 and 10, an exemplary compression screw 210 includes a head 212 and a shaft 214 extending from the head. The head 212 includes a dome 215 that transitions into a rounded or tapered circumferential surface 216 that operates to decrease the cross-section of the head from proximal to distal, where the distal aspect transitions into the shaft. Extending through the dome 215 is an opening 218 that extends through the head 212 and into a head end 220 of the shaft 214. In exemplary form, the opening 218 is defined by a series of six alternating semicircular walls 220 and six straight walls 222 that form a hexagonal pattern. At the base of the walls 220, 222 is a conical wall 224 that defines a conical part of the opening 218 terminating in the head end 220 of the shaft 214. An exterior surface 226 of the shaft 214 includes helical threads 228 that are adapted to engage a biologic substrate (not shown), such as bone. The threads 228 extend along the shaft 214 until reaching a tapered projection 230 at a far end of the screw 210.

Figure 11:
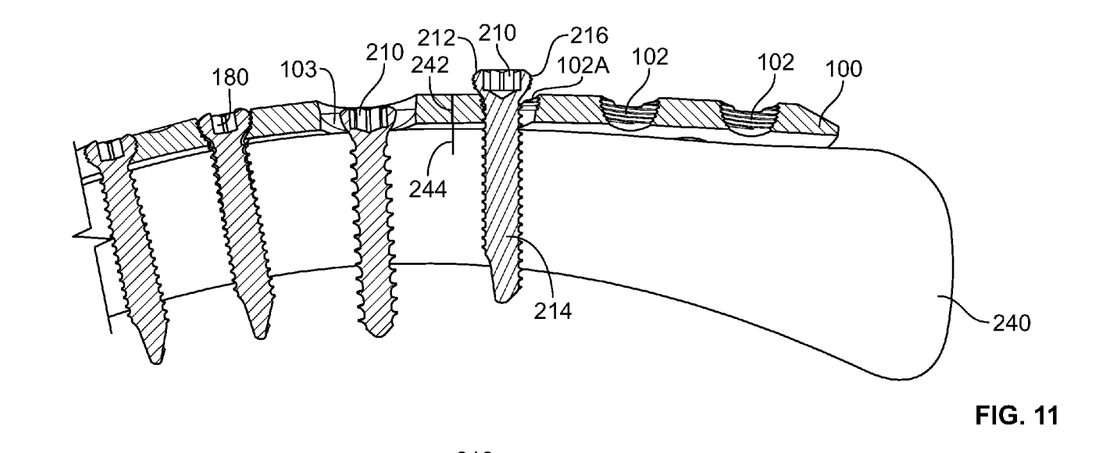
FIG. 11 is a vertical cross-section of the exemplary bone plate of FIG. 1 in position with respect to a bone, where a compression screw is partially inserted into the combination locking and compression screw hole.
Figure 12:
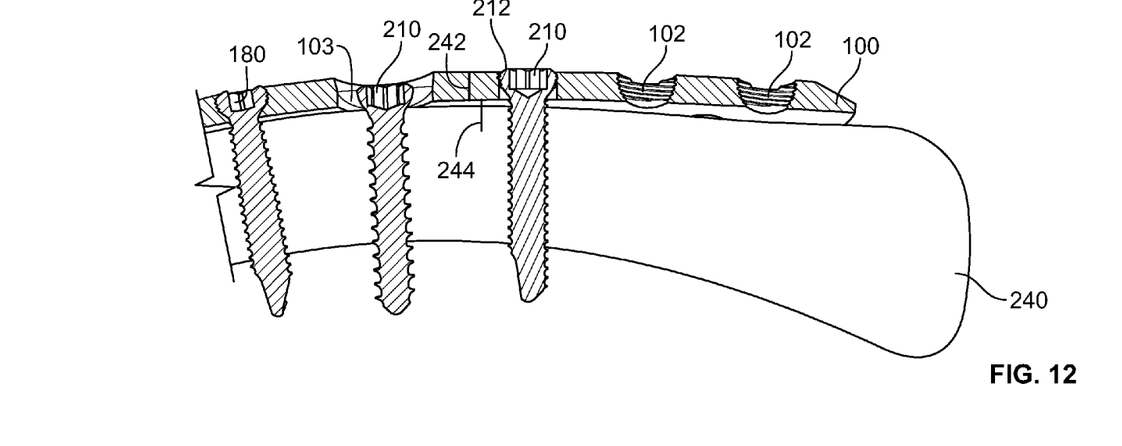
FIG. 12 is a vertical cross-section of the exemplary bone plate of FIG. 1 in position with respect to a bone, where a compression screw is fully inserted into the combination locking and compression screw hole in order to shift the position of the plate and compress the bone.

Referring to FIGS. 11 and 12, the hybrid holes 102A of the exemplary bone plate 100 may be utilized to receive a compression screw 210 in order to exert a compressive force on the bone 240. In exemplary form, a bone or bone fragments 240 is mounted to the bone plate 100 using a combination of compression and locking screws 210, 180. Presuming a surgeon finds it desirable to provide compression using the hybrid hole 102A, a pilot hole may be drilled to receive a compression screw 210. By way of example, the pilot hole is offset distally with respect the axial center of the hole 102A, which allows for the compression screw 210 to be axially offset from the center of the hole (see FIG. 11). When the compression screw 210 is initially inserted, the smaller diameter threaded shaft 214 is aligned with the pilot hole and extends through the hybrid hole 102A with the shaft contacting, but not actively engaging the threads on the side of the hole 102A. A pair of reference lines 242, 244 denotes the position of the bone 240 with respect to the bone plate 100 prior to compression. As the screw 210 is inserted farther into the bone 240, the circumferential surface 216 of the head 212 initially comes in contact with the top of the hole 102A.

When the circumferential surface 216 of the head 212 comes in contact with the top of the hole 102A, further insertion of the head is operative to push the head against the distal wall of the hole. This causes the position of the bone plate 100 to shift distally with respect to the bone 240, thereby creating a compressive force on the bone in the distal direction. As can be seen in FIG. 12, the reference lines 242, 244 are no longer aligned, as the reference mark 242 for the plate 100 has shifted distally with respect to the reference mark for the bone 240.

Figure 13:
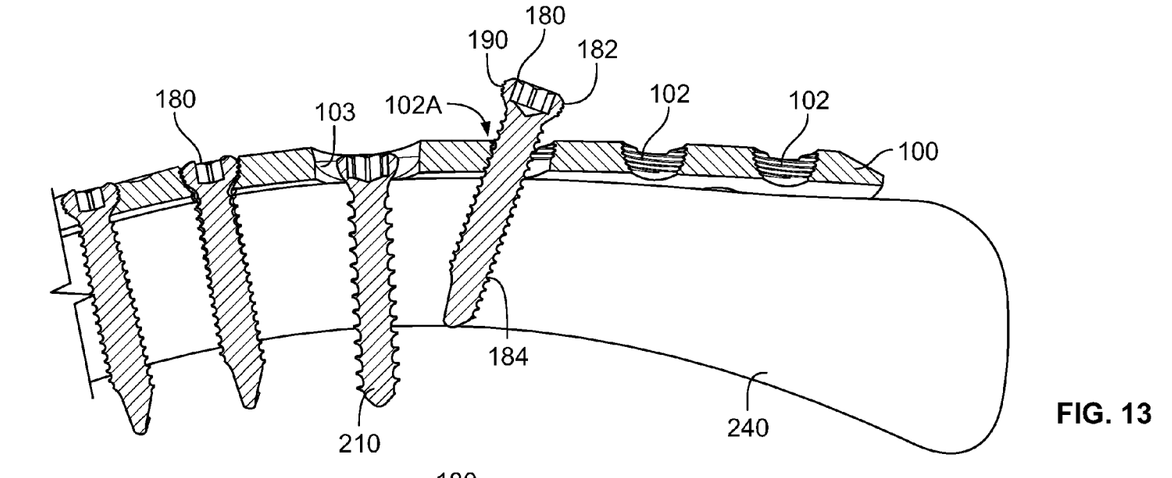
FIG. 13 is a vertical cross-section of the exemplary bone plate of FIG. 1 in position with respect to a bone, where a locking screw is partially inserted into the combination locking and compression screw hole.
Figure 14:
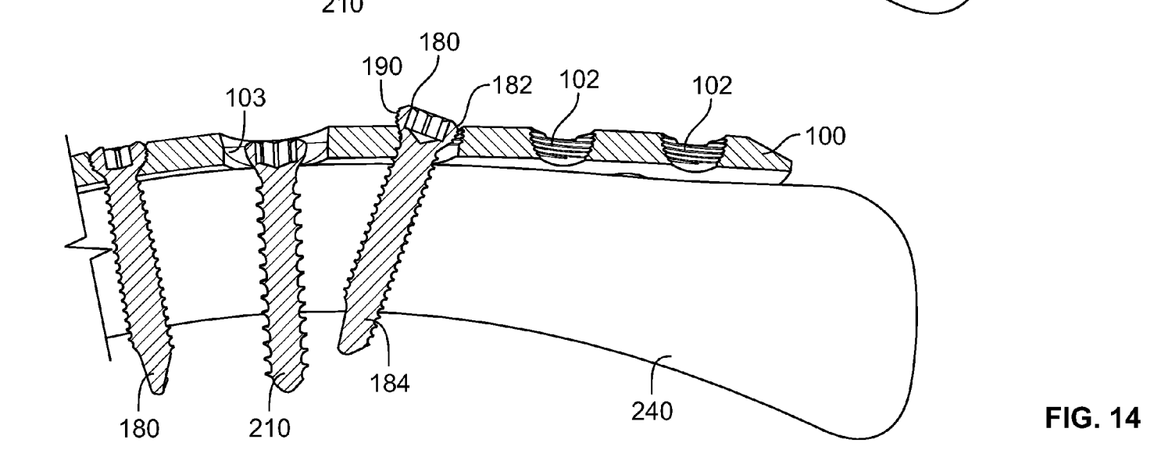
FIG. 14 is a vertical cross-section of the exemplary bone plate of FIG. 1 in position with respect to a bone, where a locking screw is fully inserted into the combination locking and compression screw hole in order to lock the angular position of the screw with respect to the plate and bone.

Referring to FIGS. 13 and 14, the hybrid holes 102A of the exemplary bone plate 100 may be utilized to receive a locking screw 180, such as a variable angle locking screw, in order fix the position of the bone plate 100 with respect to the bone 240 where screw angles other than perpendicular may be desired. In exemplary form, a bone or bone fragments 240 is mounted to the bone plate 100 using a combination of compression and locking screws 210, 180. Presuming a surgeon finds it desirable to mount the plate 100 to the bone 240 using a locking screw at an angle other than perpendicular (perpendicular could also be used as well), a pilot hole may be initially drilled. By way of example, the pilot hole is angled based upon the orientation of the bone or bone fragments 240. After the hole is drilled, a locking screw 180 is inserted through the hole 102A so that the smaller diameter threaded shaft 184 is aligned with the pilot hole. Thereafter, the locking screw 180 is rotated to fasten the screw to the bone 240, while at the same time pulling the head 182 into contact with the bounds of the hole 102A. Specifically, the threads 190 of the screw head 182 engage the threads 120 on the interior of the hole 102A in order to lock the angular position of the screw head (and screw) with respect to the bone plate 100.

It should be noted that the dimensions set forth for the exemplary embodiments are just that, exemplary. Deviations from these dimensions may be made without departing from the scope and spirit of the instant disclosure. For example, the holes 102 may have an upper diameter larger or smaller than 0.205 inches. Likewise, the holes may not necessarily have a circular cross-section at any point. Moreover, the holes may generally take on any dimensions that provides for dual functionality and use as both a compression hole and a locking hole.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A bone plate including a hybrid through screw hole, where the hybrid through screw hole includes a top opening and a bottom opening, the top opening defining a first cross-section having a circular shape at a top surface of the bone plate and including a widthwise dimension and a lengthwise dimension normal to the widthwise dimension, and the bottom opening defining a second cross-section having an oblong shape at a bottom surface of the bone plate, wherein an interior wall of the bone plate extends between the top opening and the bottom opening, the interior wall having a threaded first portion extending from the top opening and an unthreaded second portion proximate the bottom opening, the threaded first portion of the interior wall being tapered inwardly between the top surface of the bone plate and the unthreaded second portion of the interior wall, and where at least one of the widthwise dimension and the lengthwise dimension is decreased between the top opening and the bottom opening, while the other of the widthwise dimension and the lengthwise dimension does not substantially decrease between the top opening and the bottom opening.

2. The bone plate of claim 1, wherein:
the unthreaded second portion of the interior wall includes a smooth vertical surface.

3. A bone plate comprising a combination compression and locking through hole, the through hole including a top opening and a bottom opening, where the through hole includes a threaded and inwardly tapered first portion extending from the top opening and a vertically disposed second portion adjacent to the threaded first portion and proximate the bottom opening, wherein the threaded first portion defines a circular, horizontal cross-section and the second portion defines an oblong, horizontal cross-section, where the circular, horizontal cross-section and the oblong, horizontal cross-section lie along differing planes perpendicular to a central axis extending through the combination compression and locking through hole.

4. The bone plate of claim 3, further comprising a plurality of combination compression and locking through holes, where each of the plurality of combination compression and locking through holes includes a first portion including a circular, threaded horizontal cross-section and a second portion including an oblong, horizontal cross-section.

5. The bone plate of claim 3, wherein the vertically disposed second portion is unthreaded.

6. The bone plate of claim 3, wherein:
the threaded and inwardly tapered first portion includes a diameter D;
the vertically disposed second portion includes a maximum length L; and,
the diameter D is approximately equal to the length L.

7. A bone plate comprising a through screw hole demarcated by an interior surface of the bone plate that extends between a top opening and a bottom opening, the top opening having a continuous arcuate shape and allowing throughput of a first imaginary cylinder having a circular cross-section with a diameter D1, the interior surface having a first threaded segment extending from the top opening and tapers inwardly from a top surface of the bone plate to a stopping distance SD to inhibit throughput of the first imaginary cylinder at a location between the top opening and the bottom opening, the interior surface having a vertically disposed second segment adjacent to the first segment and proximate the bottom opening, the second segment defining an oblong, horizontal cross-section, wherein the first segment and the second segment are configured to allow throughput of a second imaginary cylinder having a circular cross-section with a diameter D2, where the diameter D1 is greater than the diameter D2, where the stopping distance SD is greater than D2, and wherein a maximum horizontal distance across the second segment is greater than 1.3 times D2.

8. The bone plate of claim 7, wherein the interior surface of the first segment includes a first circumferential curvature and the second segment includes a second circumferential curvature, wherein the first circumferential curvature is larger than the second circumferential curvature.

9. The bone plate of claim 8, wherein the second segment does not include threads.

* * * * *